United States Patent [19]
Duffy et al.

[11] Patent Number: 6,086,611
[45] Date of Patent: Jul. 11, 2000

[54] BIFURCATED STENT

[75] Inventors: Naill Duffy, Tuan; Maria Carleton, County Galway, both of Ireland; Daniele Manara, Bentivoglio, Italy; Gigliano Garutti, Poggio Renatico, Italy; James Cattabriga, Bologna, Italy; James Duffy, Trim, Ireland

[73] Assignee: AVE Connaught, Dublin, Ireland

[21] Appl. No.: 08/937,199

[22] Filed: Sep. 25, 1997

[51] Int. Cl.[7] .................................................. A61F 2/06
[52] U.S. Cl. ............................................................. 623/1
[58] Field of Search ........................................ 623/1, 12

[56] References Cited

U.S. PATENT DOCUMENTS

| | | |
|---|---|---|
| 4,896,670 | 1/1990 | Crittenden . |
| 4,969,458 | 11/1990 | Wiktor ..................................... 606/194 |
| 4,994,071 | 2/1991 | MacGregor .............................. 606/194 |
| 5,607,445 | 3/1997 | Summers ..................................... 623/1 |
| 5,653,727 | 8/1997 | Wiktor ......................................... 623/1 |
| 5,669,924 | 9/1997 | Shaknovich ................................. 623/1 |
| 5,672,169 | 9/1997 | Verbeek ...................................... 623/1 |
| 5,679,659 | 10/1997 | Verhoeven et al. . |
| 5,720,735 | 2/1998 | Dorros . |
| 5,725,572 | 3/1998 | Lam et al. . |
| 5,749,825 | 5/1998 | Fischell et al. . |
| 5,755,734 | 5/1998 | Richter et al. . |
| 5,755,735 | 5/1998 | Richter et al. . |
| 5,755,771 | 5/1998 | Penn ............................................ 623/1 |
| 5,766,238 | 6/1998 | Lau et al. . |
| 5,769,885 | 6/1998 | Quiachon ................................... 623/1 |
| 5,769,887 | 6/1998 | Brown ........................................ 623/1 |
| 5,782,906 | 7/1998 | Marshall et al. . |
| 5,824,042 | 10/1998 | Lombardi et al. . |
| 5,824,043 | 10/1998 | Cottone, Jr. . |
| 5,824,056 | 10/1998 | Rosenberg . |
| 5,851,228 | 12/1998 | Pinheiro ..................................... 623/1 |
| 5,855,598 | 1/1999 | Pinchuk . |

FOREIGN PATENT DOCUMENTS

| | | |
|---|---|---|
| 0 421 729 | 4/1991 | European Pat. Off. . |
| 0 669 114 | 8/1995 | European Pat. Off. . |
| WO 95/21592 | 8/1995 | WIPO . |
| WO 96/41592 | 12/1996 | WIPO . |

*Primary Examiner*—Michael J. Milano
*Attorney, Agent, or Firm*—Sterne, Kessler, Goldstein & Fox P.L.L.C.

[57] ABSTRACT

An endoluminal stent is formed in a modular construction to include at least one elongate spine and a plurality of general tube-defining modules attached to the spine, or spines, in a longitudinal array. The modules are constructed along a spine-like structure so as to form a bifurcate shape for implantation in branching or bifurcating vessels. Each module defines, in cooperation with a spine, a closed ring-like structure. Each of the modules is radially expandable from a reduced diameter, low profile configuration, in which it is readily navigated through the body passages, to an expanded diameter engageable with the inner luminal surface of the body lumen. The stent, being of modular construction, can be built to individual specifications for a specific patient. Modules are formed from a wire shaped in a flat serpentine configuration that is then wrapped in a cylindrical configuration with its free ends connected to a spine. The modules are expandable, as by a balloon, from a low profile to an expanded configuration. During expansion, the modules can wipe against the inner surface of the lumen to smooth sharp points or edges. A spine of the stent defines a substantially greater mass than that of the individual modules such that the spine can be readily observed under X-ray or fluoroscopy. The modular construction enables a wide range of variation in the characteristics of the stent, including longitudinal flexibility, radial expansion characteristics, among others.

21 Claims, 10 Drawing Sheets

POSITION STENT AND DELIVERY SYSTEM

Fig. 6C

AFTER DEPLOYMENT

3.5 Ø BALLOON

Fig. 7A

AFTER FIRST INFLATION

Fig. 7B

POSITION 5.5

Fig. 7C

INFLATE 5.5

Fig. 7D

DEFLATE, REMOVE BALLOON AND GUIDEWIRES

Fig. 7E

BIFURCATED STENT

BACKGROUND OF THE INVENTION

A number of medical procedures involve or can be supplemented with the placement of an endoluminal prostheses, commonly referred to as a stent, that can be implanted in a lumen, such as a blood vessel or other natural pathway of a patient's body. Such stents typically define a generally tubular configuration, and are expandable from a relatively small diameter (low profile) to an enlarged diameter. While in its low profile configuration, the stent is advanced endoluminally, by a delivery device, through the body lumen to the site where the stent is to be placed. The stent then can be expanded to a larger diameter to firmly engage the inner wall of the body lumen. When the stent is delivered satisfactorily the delivery device is removed, leaving the implanted stent in place. In that manner, the stent may serve to maintain open a blood vessel or other natural duct, the functioning of which had become impaired as a result of a pathological or traumatic occurrence.

Among the medical procedures in which stents have had increasing use is in connection with percutaneous transluminal angioplasty (PTA), and particularly percutaneous transluminal coronary angioplasty (PTCA). PTA and PTCA involve the insertion and manipulation of a dilating catheter through the patient's arteries to place the dilatation balloon of the catheter within an obstructed portion (stenosis) of a blood vessel. The balloon is expanded forcibly within the obstruction to dilate that portion of the blood vessel, thereby restoring blood flow through the blood vessel. Among the more significant complications that may result from such angioplasty is when the dilated site becomes obstructed again, for example, by restenosis. By placing a stent within the blood vessel at the treated site, the tendency for such restenosis may be reduced.

Stenoses may often develop in the branching region of a patient's blood vessel. Treatment of a stenosis in the branched region may present numerous additional difficulties in the design of devices to dilate stenoses at the branched region. Techniques and devices have been developed to effect a dilatation at a branched region such as the "kissing balloon" technique described in U.S. Pat. No. 4,896,670, or pending Bard patent "Dual Balloon System." The need for an effective stent that can be placed at a bifurcated region has been recognized.

SUMMARY OF THE INVENTION

The invention includes, inter alia, stents, methods for making stents, and procedures for treating restenosis and other conditions suitable for treatment by application of an endoluminal prosthesis. The stents described herein can include, but are not limited to, bifurcated stents constructed in a modular fashion and having at least one elongate spine suitable for disposition within a vessel. The spine can attach to a plurality of generally tubular modules to form a longitudinally sequenced array of such modules. Each module can define, in cooperation with its associated spine, a closed, ring-like structure, with the modules being aligned in an array to define a cage-like, generally tubular structure. Each of the modules may be formed from wire and is radially expandable from a reduced diameter, low profile configuration to an expanded diameter profile suitable for engaging with the inner luminal surface of a blood vessel or other body lumen. Each spine can include a longitudinal support wire to which the modules may be individually mounted in succession.

In one embodiment, the bifurcated stent is composed of three sections, one main body and two side branch sections. Each section can define a single tubular configuration having its own array of modules connected to and extending along at least one spine. The main body of the stent is connected to the two side branch sections by means of one or more spines and/or by means of the modules.

In one practice, the stents described herein can be placed onto a dual balloon catheter delivery system, or onto two balloon catheters and, while in the low profile configuration, can be advanced to a bifurcated vessel. A delivery system incorporating a protective retractable covering sleeve over the stent may also be employed. The stent can be deployed by applying a radial force to the modules, optionally by inflation of a balloon catheter.

Among the objectives of the invention is to provide an easily placable bifurcated endovascular stent.

Another object of the invention is to provide a bifurcated stent that can be placed in the coronary arteries as well as other branched vessels.

Another object of the invention is to provide a bifurcated stent that can be tailored to the vascular anatomy of the patient in whom the device is to be implanted.

Another object of the invention is to provide a bifurcated stent of which a region of the bifurcate stent, for example the region nearest the apex region of the branching vessel, can be independently tailored to suit the particular vessel.

A further object of the invention is to provide a bifurcated stent having good radiographic characteristics to facilitate placement and subsequent visualization of the stent.

Another object of the invention is to provide a bifurcated stent construction that is modular.

Another object of the invention is to provide a bifurcated stent that can be used as a scaffold for a PTFE, or other, graft for peripheral & coronary applications.

DESCRIPTION OF THE DRAWINGS

The foregoing and other objects and advantages of the invention will be appreciated more fully from the following description thereof, with reference to the accompanying drawings wherein.

DESCRIPTION OF THE ILLUSTRATIVE EMBODIMENTS

Figure 1A:
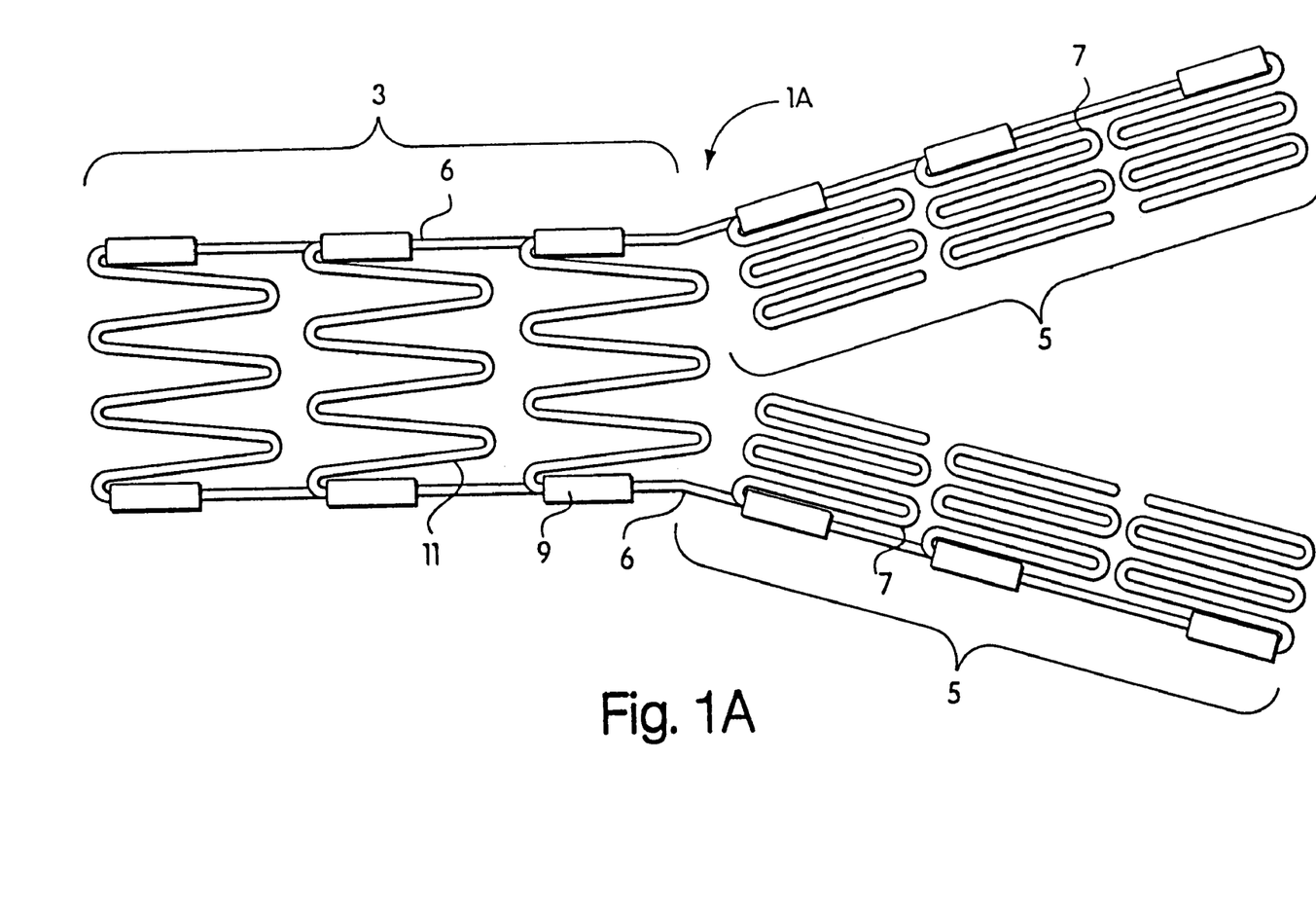
FIG. 1(a) is a side illustration of one bifurcate stent in a deployed configuration.
Figure 1B:
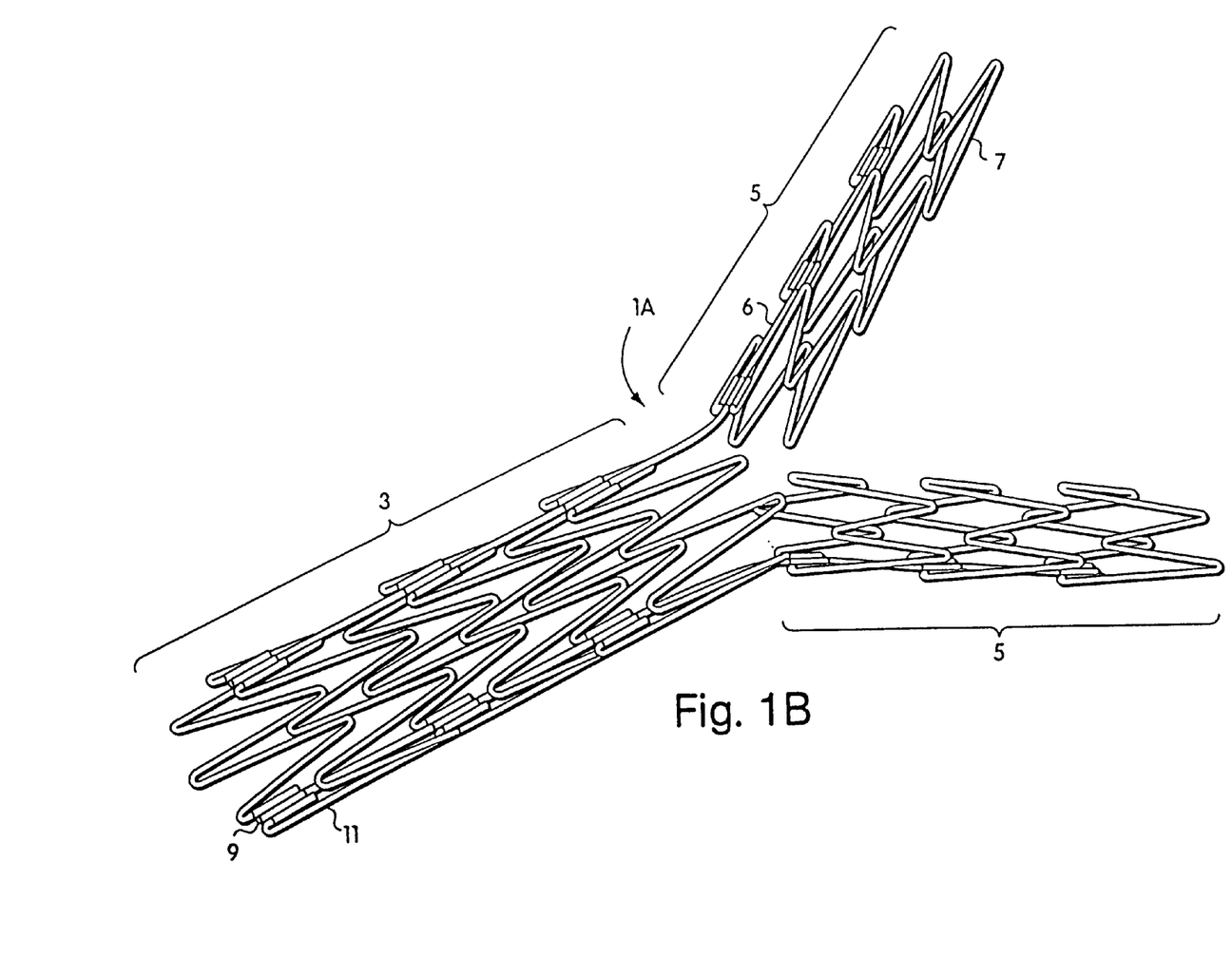
FIG. 1(b) provides an oblique perspective of one bifurcate stent in a deployed configuration.
Figure 2:
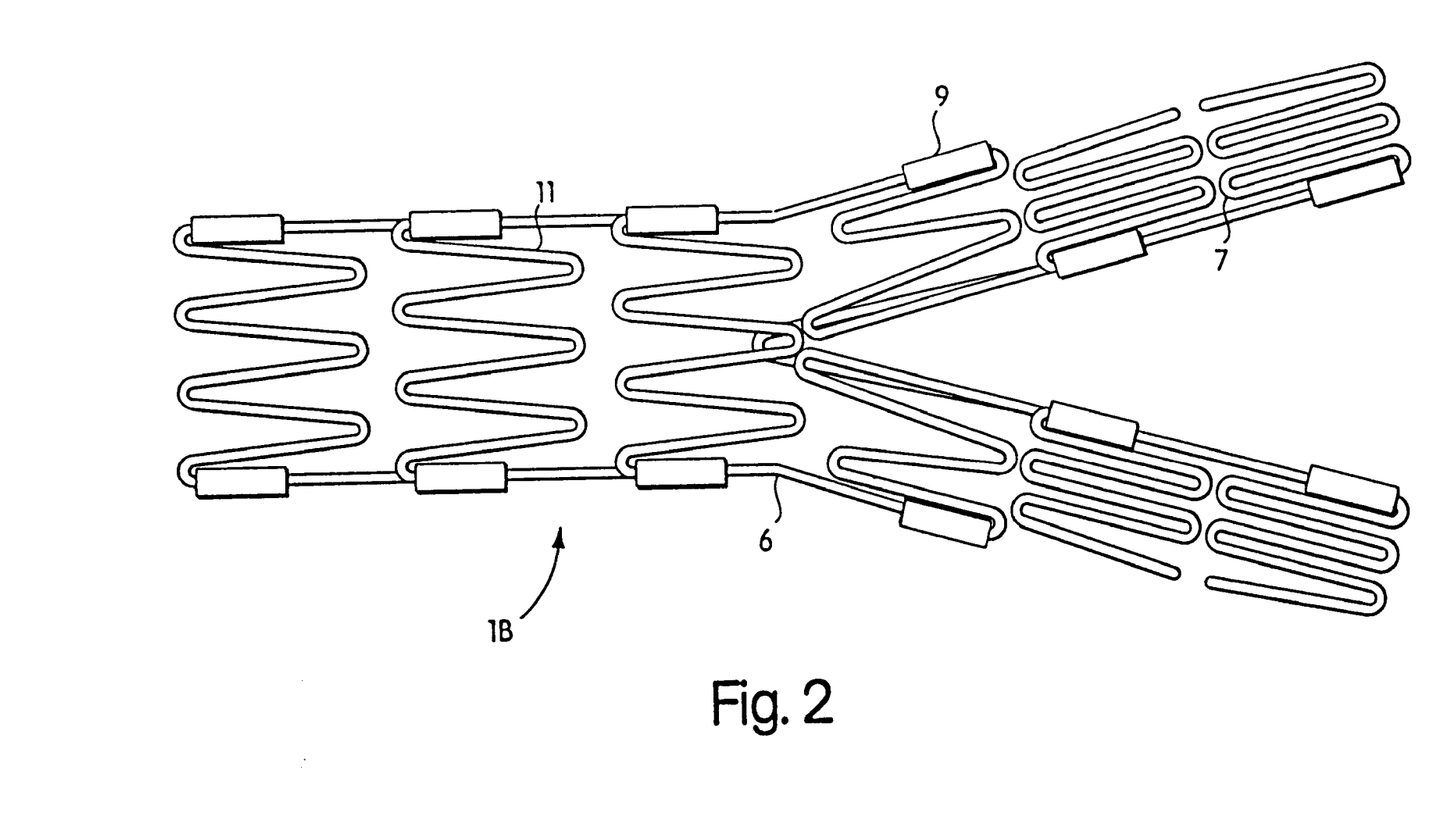
FIG. 2 is a side illustration of one bifurcate stent in a deployed configuration with an alternative arrangement of spines in the side branches.
Figure 3:
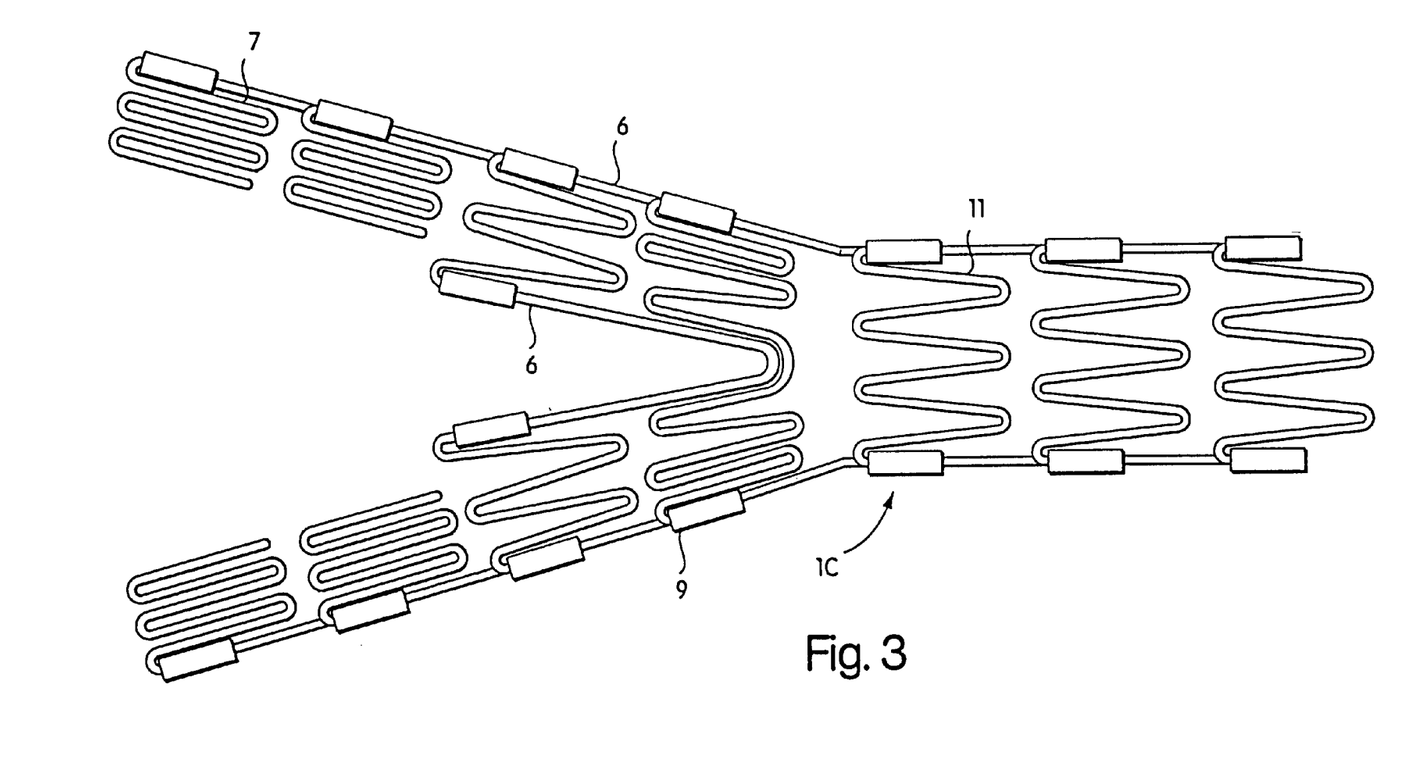
FIG. 3 is a side illustration of one bifurcate stent in a deployed configuration with a modified apex section to provide more wall coverage at the apex section of the branched vessel.
Figure 4:
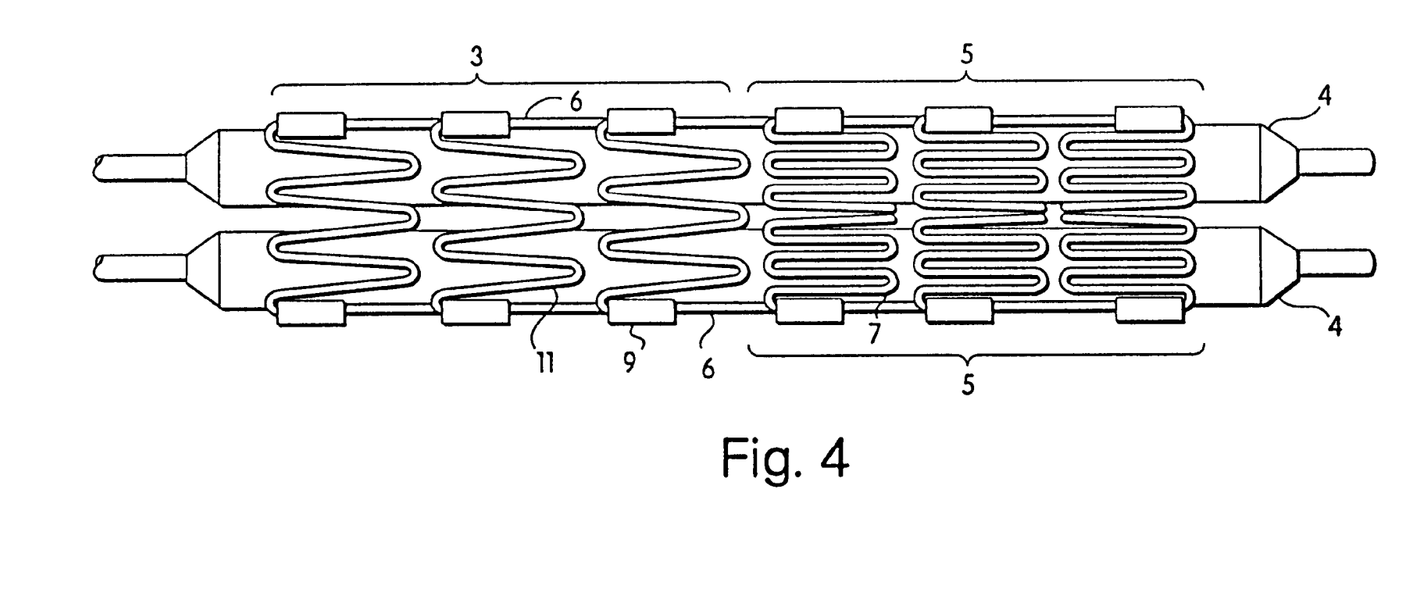
FIG. 4 is a diagrammatic illustration of a stent of the type depicted in FIGS. 1–3 carried on two balloons while in a low profile configuration.

FIGS. 1(a)–(b) illustrate one type of modular endoprosthesis, a stent, that may be employed in practicing the invention. In particular, FIG. 1(a) depicts a stent having a main body 3 formed of modules 11 and connectors 9, and side branches 5 formed of side branch modules 7, and connectors 9. The depicted stent includes two support wires 6, each of which extends substantially from the proximal end to the distal end of the stent. For clarity, the terms "proximal" and "distal" can be understood from the stent of FIG. 1(a) and from the definition that the main body 3 is proximal of the side branches 5. FIG. 1(a) further depicts that each of the support wires 6 extend along the sidewall of the main body 3, branching off at the apex formed where the side branches 5 join the main body 3. FIG. 1(a) further depicts that each support wires 6 attaches to a respective one of the side branches 5, and continues on distally, to provide a spine along the sidewall of the respective side branch 5. The support wires 6 connect the main body 3 to each of the side branches 5. Optionally, one or more of the support wires 6 can be formed from a flexible or resilient material, thereby allowing the side branches 5 to be brought together from the opened configuration of FIG. 1(a), to the closed configuration depicted in FIG. 4. Additionally, a resilient as support wire 6 can be biased in the open configuration of FIG. 1(a), such that the support wires 6 will tend to move the stent from the closed configuration of FIG. 4, to the open configuration of FIG. 1(a).

The endoprosthesis may be considered to define a cage-like tubular arrangement formed from wire-like components and having a main body section 3 and two side branch sections 5. The stent depicted in FIGS. 1(a)–(b) is constructed from a plurality of individual modules, containing main body modules 11 and side branch modules 7 connected to each other along at least one spine that may be considered to include a longitudinal support wire 6 and connectors 9. The modules 7 and 11 are expandable from a contracted, low profile configuration, to facilitate placement of the stent in the body lumen, to an enlarged diameter in which the modules can be brought into firm engagement with the inner surface of the walls of the body lumen to maintain the body lumen open to facilitate blood flow. In the one optional embodiment, the modules are expandable inelastically. The radially expandable generally tubular modules 7 and 11 are mounted and aligned in longitudinally sequenced array on the support wire 6 by a connector 9 associated with each of the modules 7 and 11. As detailed in FIG. 5(b), the modules 7, when mounted on a support wire 6, may be considered to define a virtual peripheral surface 12, that, in transverse cross-section, is in the form of a virtual closed curve or loop 8 about the longitudinal axis 2. Likewise the modules 11 in the main body 3, when mounted on at least one support wire 6, may also be considered to define a virtual peripheral surface.

Each module 7 and 11 can be formed from a wire 13 shaped and configured to enable radial expansion of the cylindrical peripheral surface 12. The module may be formed by first forming the wire 13 into a flat serpentine configuration and then wrapping the serpentine wire into its looped configuration. The terminal ends 16 of the serpentine wire 13 are free. The free ends 16 of the wire 13 may be attached to each other and to the support wire 6 by the connector 9. The serpentine arrangement of each of the modules may be considered to include a series of elongate segments alternated with and connected by bends that may be curved (e.g., circular) or may comprise shorter connective segments 15 connected to the elongate segments 14 at cusps 17. The connective bends between the longitudinal segments 14 may lie along and define a locus of the closed loop 8. Preferably, the wire 13 is formed so that the arrangement of bends will be uniformly circumferentially spaced about the virtual closed loop 8 to provide the modules 7 and 11 with uniform strength in directions transverse to the support wire or wires 6.

Figure 5A:
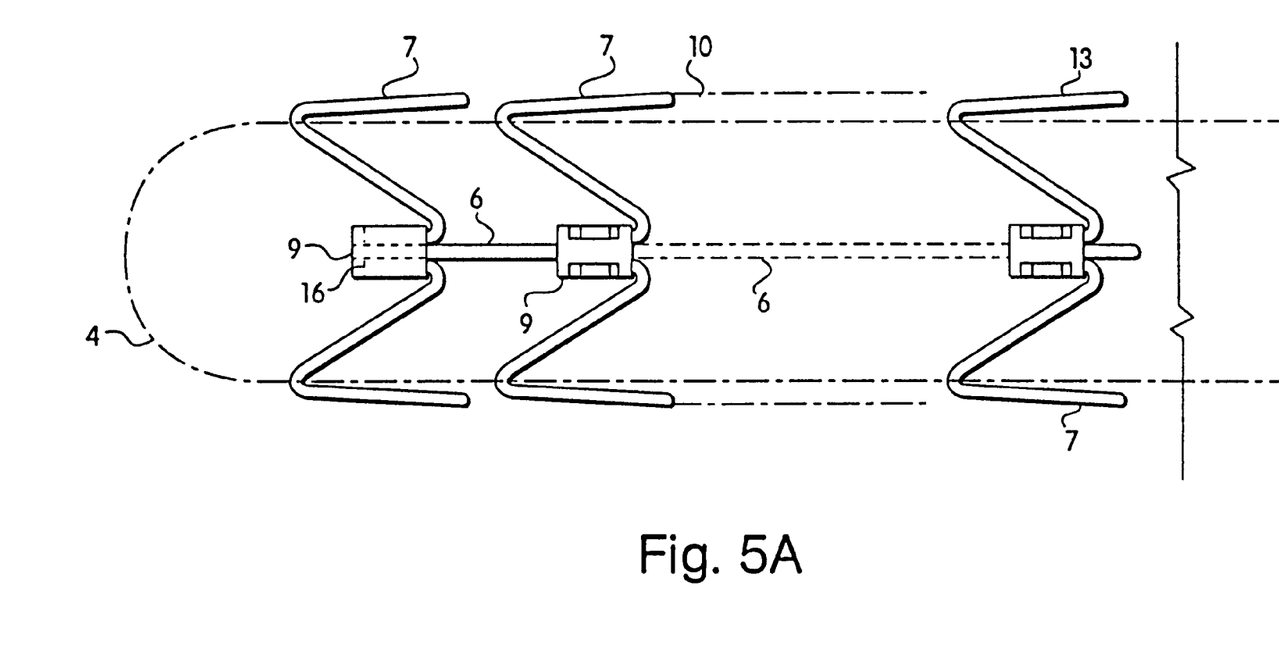
FIGS. 5(a)–(c) are diagrammatic illustrations of modules of the stent illustrating a possible connection to a support wire and some examples of different module configurations.
Figure 5B:
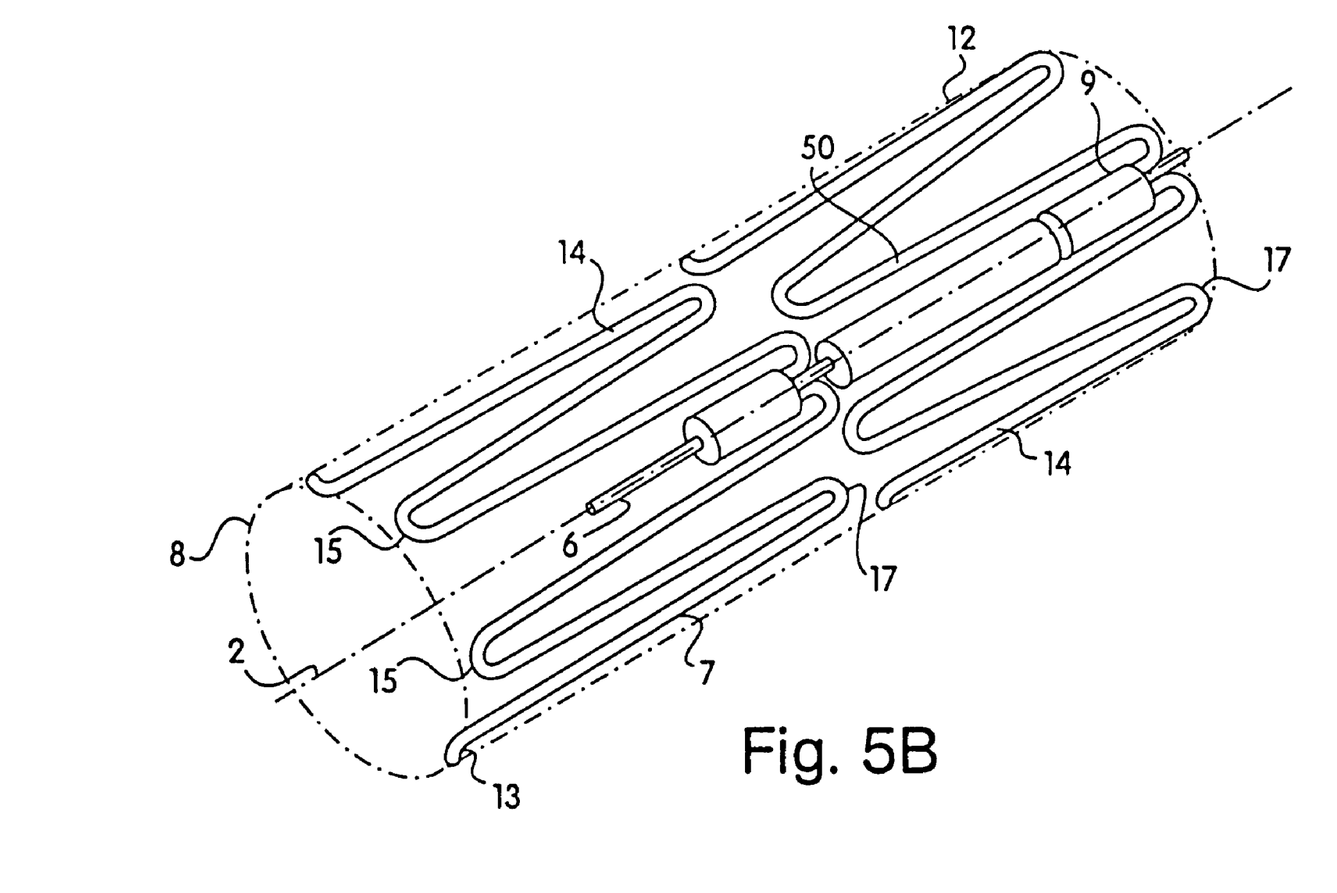

As illustrated in FIG. 5(b) when the modules are in their low profile, unexpanded configuration, the bends 15, 17 that define the connection between adjacent longitudinal segments are such that the elongate segments 14 will lie substantially parallel to each other, defining an angle close to zero degrees. The angle will increase when the module is expanded, as shown in FIG. 5(a). The configuration of the connective bends, including the cusps 17 may be varied to vary the angle or to vary their number circumferentially about the closed loop 8 to vary the characteristics of the modules 7 and 11, including varying its resistance to compressive radial loads such that the endoprosthesis can further be tailored and made to conform ideally to the specific body lumen in which it is to be implanted.

By way of illustrative example only, a stent may be provided to include modules 7 formed from wire having a diameter of about 0.15 millimeter with elongate segments 14 (not including the connective bends between adjacent segments 14) of a length of about 1.8 millimeters. When the connective bends between adjacent elongate segments 14 are smoothly curved, they may have a radius of about 0.15 millimeter before expansion. A stent having the foregoing dimensions can be expected to be expandable to diameters between about 2.5 to about 4.0 millimeters without excessive expansion, and that such stent exhibits substantial resistance to radial collapse that can be well above the maximum radial compressive loads and can be expected to be imposed on the stent by contraction of an artery having a luminal diameter of about 2.5 to about 4.0 millimeters.

Again by way of illustrative example only, a stent may be provided to include modules 11 formed from wire having a diameter of about 0.15 millimeter with elongate segments 14 (not including the connective bends between adjacent segments 14) of a length of about 2.7 millimeters. When the connective bends between adjacent elongate segments 14 are smoothly curved, they may have a radius of about 0.15 millimeter before expansion. A stent having the foregoing dimensions can be expected to be expandable to diameters between about 3.0 to about 5.5 millimeters without excessive expansion, and that such stent exhibits substantial resistance to radial collapse that is well above the maximum radial compressive loads and can be expected to be imposed on the stent by contraction of an artery having a luminal diameter of about 3.0 to about 5.5 millimeters.

In one embodiment, the connectors 9 may be constructed to be mounted on the longitudinal support wire 6 by threading them on the wire 6. The connector 9 preferably may comprise a ring that defines sufficient internal space to receive and circumscribe the free ends 16 of the wire 13 while also permitting firm connection of the ring to the longitudinal support wire 6. The connector 9, free ends 16 of the wire and support wire 6 may be firmly connected by means of a permanent deformation, for example, by crimping, or may be attached to each other by spot welding. When assembled using laser spot welding, it is preferred that the terminal portions 16 of the module 7 or 11 are first welded to the connector(s) 9 and the connector(s) 9 then is welded to the support wire 6. In some instances, it may be desirable to modify the stent so that one or more of the modules (but typically not the endmost modules) are not securely attached to the support wire but, instead, are permitted some freedom of sliding movement along the support wire. This may enable making of a final adjustment to the position of the module after the device has been placed in the patient's blood vessel, should that be desired.

Connector 9 may be in the form of a relatively short segment of a tube receptive to the support wire 6 and the free ends 16 of the modules 7 and 11. The internal surface of the connector 9 may be contoured to closely match the contour defined by the support wire 6 and free ends 16 that pass through the connectors 9, thus in effect preforming the connector.

The foregoing construction enables a stent to be specially assembled to conform precisely to the specific anatomy of the patient in whom the stent is to be placed. The modules can be positioned as desired along the support wire 6 and can be secured in that configuration. The support wire 6 may be selected to provide the desired degree of longitudinal flexibility and may be made from wire that is extremely flexible to aid in each of positioning of the device. With the foregoing construction in which the stent has at least one independent support wire 6 in each section, the degree of stiffness or flexibility of the support wire can be selected independently of the wire from which the tubular modules 7 are formed. The support wire 6 may be highly flexible to aid the stent to be carried through tortuous vessels, such as coronary arteries.

It should be understood that although the presently preferred embodiment of the invention incorporates a metal support wire 6 (e.g., stainless steel), the modular construction of the invention enables a fabrication of a stent in which the support wire may be formed from nonmetallic materials, such a polymeric materials, for example, nylon. Other mechanically and biologically suitable classes of materials may be selected, including materials from among those that are biologically absorbable into the tissue of the vessel wall over time. With a bioabsorbable support wire 6, it should be selected to maintain its desirable mechanical characteristics for a sufficient time to enable the modules 7 to become firmly embedded in the vessel wall. Thus, the modular construction of the invention provides a substantially increased range of materials and properties for the individual components, each being selected to provide optimum results.

Connectors 9, especially when assembled about the two end segments 16 of the modules 7 and 11 and the support wire 6, present a significantly greater mass than that of the wire 13 from which the modules are fashioned. Thus, the region of the spine that includes the Connectors 9 will present substantially greater radiopacity than that presented by the wire 13 of the associated module. The substantially increased radiopacity of the connected region enhances substantially the radiographic control of the endoprosthesis 1(a)–(c) during implantation. It also enables the prosthesis to be observed radiographically at a later time without requiring use of ultrasound procedures. The configuration of the stent enables the tubular frame 10 to be constructed to have a high mechanical strength while enabling expansion of the device between its low profile and maximum expanded alloys, and titanium-chromium alloys.

The support wire 6 and modules may be treated and formed to vary the mechanical and functional characteristics independently of each other to obtain a desired configuration adapted to treat the anatomy of a specific patient. For example, the wire 13 from which the module is formed may be subjected to an annealing heat treatment to control the malleability of the wire.

Also among the characteristics of the invention is the manner in which the tubular modules 7 protect the balloon of a balloon catheter 4 (FIG. 4) used in the placement of the endoprosthesis 1(a)–(c). When the device if mounted on the folded balloon of the catheter and is in its low profile phase adapted for delivery, the elongate segments 14 will be disposed in close substantially parallel proximity to each other circumferentially about the balloon. Additionally, to the extent that the individual tubular modules can be arranged in close longitudinal proximity to each other the balloon can be fully protected within the stent longitudinally as well as circumferentially. After the device and catheter 4 have been navigated to locate the deployment site, expansion of the device can cause the elongate segments 14 to spread and expand circumferentially along the walls to the body lumen to wipe against the walls and smooth surface roughness that may be present including, particularly, smoothing of sharp or hard regions that otherwise could damage the balloon and possibly result in balloon puncture. As the segments 14 of the module wipe against the walls of the passage, they effect a significant shearing action.

Figure 5C:
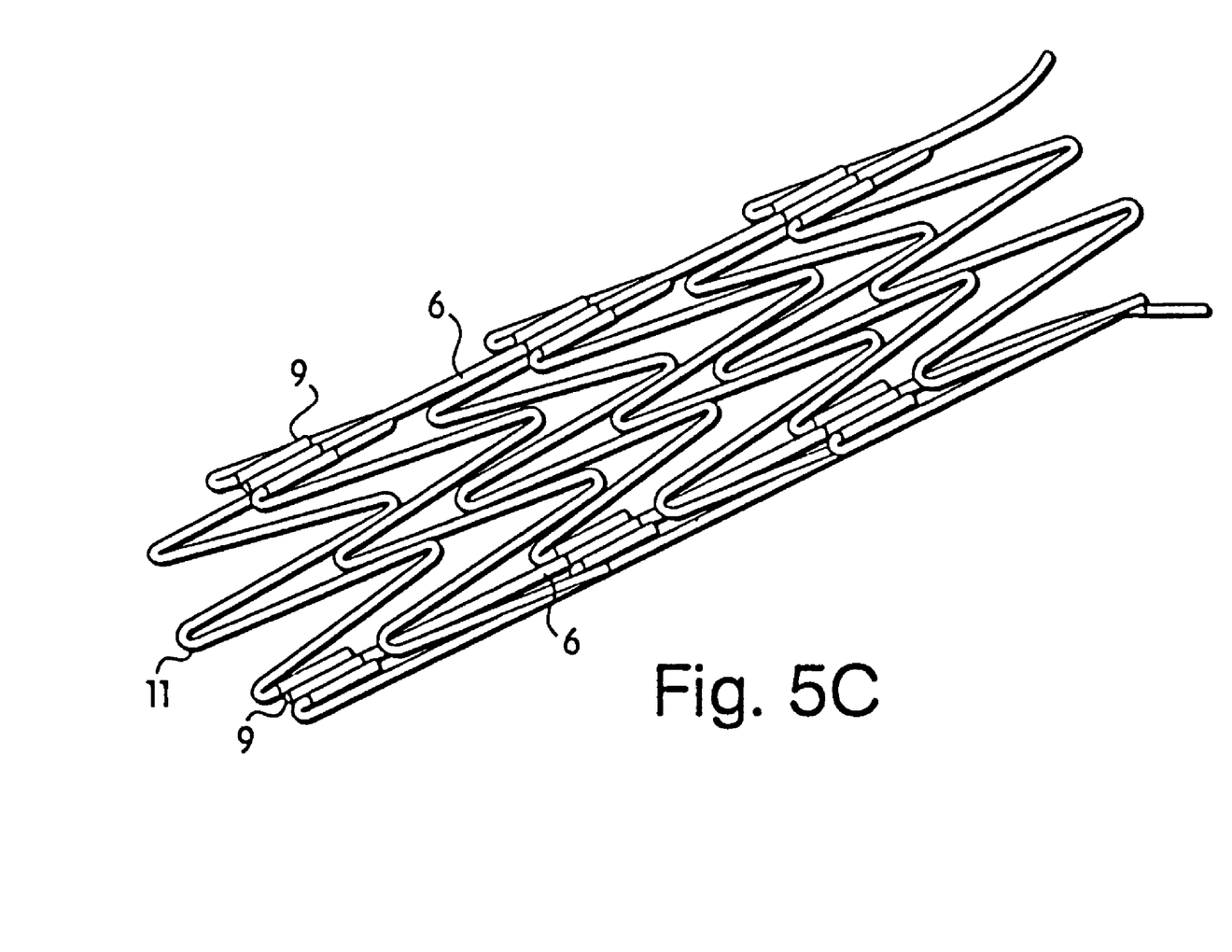

It may be noted that the main body 3 and side branch 5 sections may be constructed with multiple spines. FIG. 5(c) illustrates an arrangement in which the module is constructed using two connectors 9 and support wires 6 circumferentially spaced about the virtual periphery 12, so as to create two spines. In this embodiment, each of the wires 13 of the modules 11 is formed to circumscribe about 180° of the loop defined by the module such that they can cooperate to define the generally cylindrical configuration. The connectors 9 shown in FIG. 5(c) may be pre-formed into a shape as shown so as to aid placement of the wire 13 during manufacture.

Figure 6A:
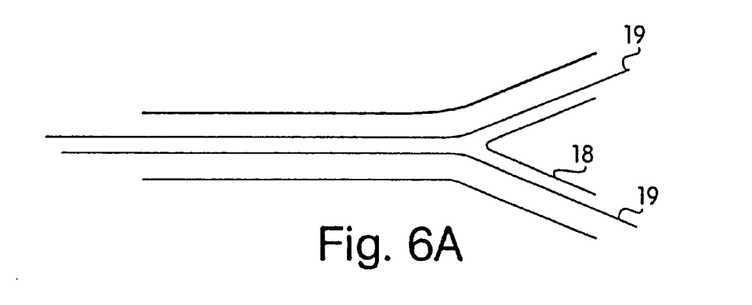
FIGS. 6(a)–(c) illustrate, diagrammatically, one manner in which a bifurcate stent can be deployed using a dual balloon arrangement.
Figure 6B:
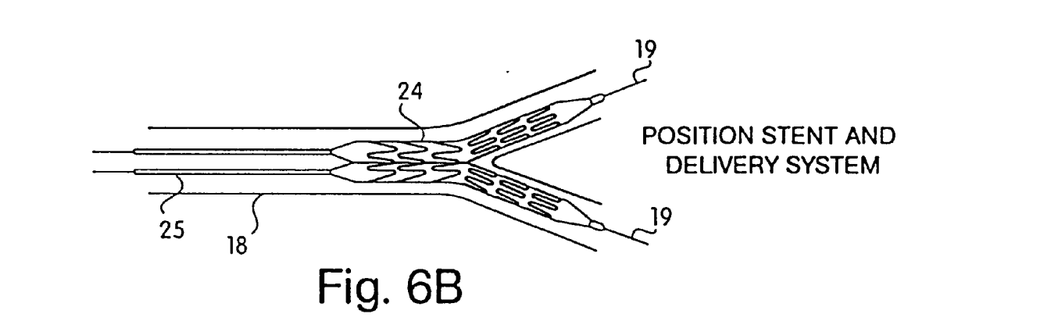
Figure 6C:
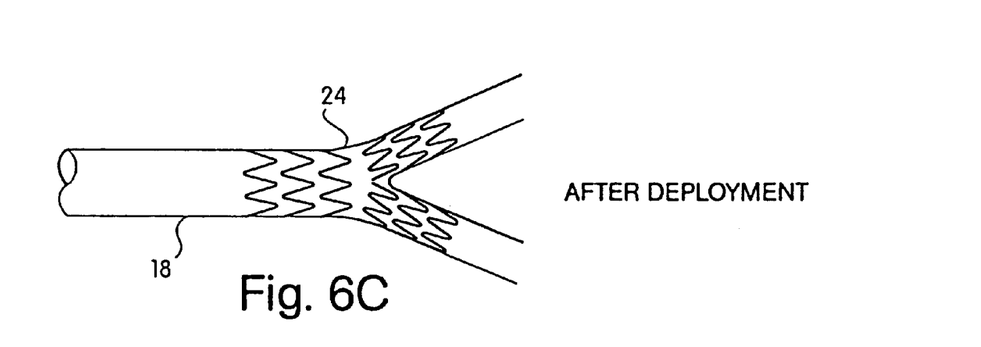
Figure 7A:
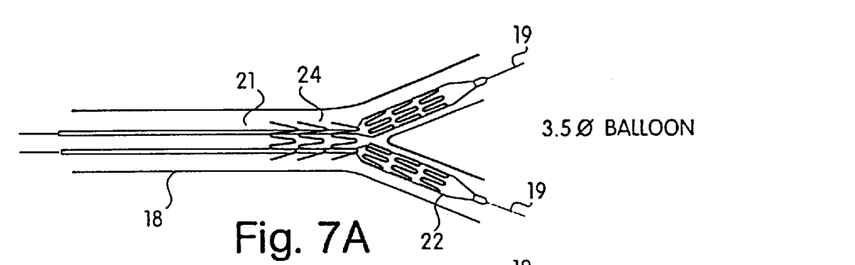
FIGS. 7(a)–(e) illustrate, diagrammatically one technique for deploying a bifurcate stent by operation of separate balloon catheters.
Figure 7B:
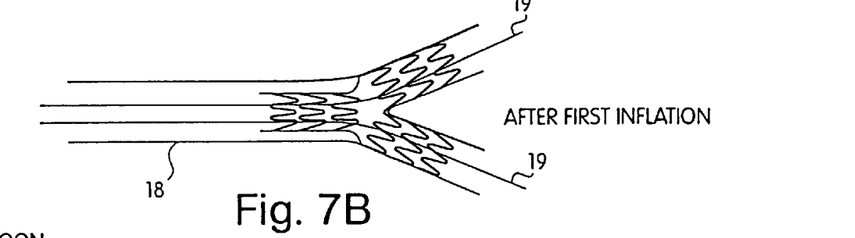
Figure 7C:
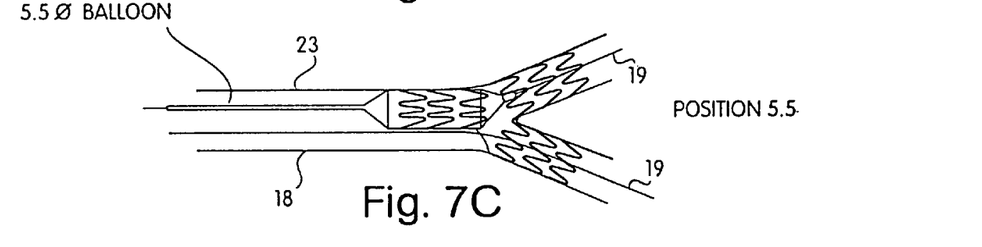
Figure 7D:
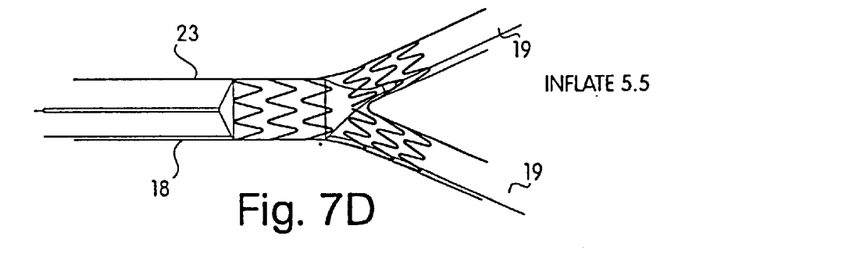
Figure 7E:
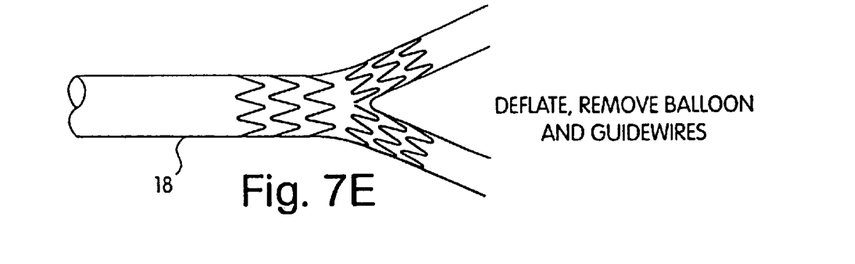

FIG. 6 illustrates a possible technique to deploy the stent, shown here as a general outline 24 to simplify the diagram and aid viewing, using a dual balloon arrangement. Two guide wires 19 are positioned in the bifurcated vessel 18 by means of the known prior art. This is illustrated in FIG. 6(a). The bifurcated stent is crimped onto the dual balloons to obtain the low profile state and the two balloons of the dual balloon catheter with the crimped stent are advanced over the guide wires to the bifurcated vessel as depicted in FIG. 6(b). The system can be advanced through a guiding catheter (not shown) to the site of the bifurcated vessel by any suitable system or method known in the art. The dual balloon catheter is now used to expand the stent to its deployed configuration by applying a radial force on the modules of the stent by means of the two balloons 25, as depicted in FIG. 6(c). The balloons 25 are now deflated and can be removed along with the guide wires 19 to leave the stent 24 in its deployed configuration.

FIG. 7 illustrates one possible technique to deploy the stent, again shown here as a general outline 24 to simplify the diagram and aid viewing, using standard balloon catheters. Two guide wires 19 are positioned in the bifurcated vessel 18 by any means known in the art. The stent is crimped down onto two separate balloons, one balloon 21, being longer than the other 22. The bifurcated stent is crimped onto the two balloons 21 and 22 to obtain the low profile state and the two balloons 21 and 22 with the crimped stent are advanced over the guide wires to the bifurcated vessel 18 as depicted in FIG. 7(a). The system can be advanced through a guiding catheter to the site of the bifurcated vessel by any suitable system or method known in the art. The two balloon catheters is now used to expand the stent 24 to its deployed configuration by applying a radial force on the modules of the stent 24 to its deployed configuration by applying a radial force on the modules of the stent 24 by means of the two balloons 21 and 22 sized to fit the side branch vessels 28, as depicted in FIG. 7(b). The balloons 21 and 22 are now deflated and can be removed. A third balloon 23, sized to fit the main branch vessel 27 can now be inserted over one of the guide wires 19, as shown in FIG. 7(d). The balloon 23 can now be deflated and can be removed along with the guide wires 19 to leave the stent 24 in its deployed configuration, as shown in FIG. 7(e).

If desired, the wires embodied in the stent 1(a)–(c) may be coated with a protective material such as carbon or with an anticoagulant substance such as heparin.

In a further alternative embodiment, the stent may be expandable by other means, for example, by forming the module 7 from a shape memory alloy such as nitinol. The stent may be provided with electrical resistance heaters to generate sufficient heat to induce thermally controlled expansion of the shape memory alloy module. A delivery system could be used to position the stent in the bifurcated vessel which would facilitate expansion of the stent after placement.

If felt necessary after deployment, post dilatation with balloons tailored to the artery could follow the stent deployment.

It should be understood that the foregoing description of the invention is intended merely to be illustrative thereof and that other embodiments, modifications and equivalents will be apparent to those skilled in the art without departing from its principles.

What is claimed is:

1. A bifurcated stent comprising:
   a main body comprising a support wire and a plurality of modules coupled to said support wire at sequential locations along said support wire, said support wire extending between and through said plurality of modules;
   a first side branch coupled to said main body, said first branch comprising at least one module coupled to a support wire; and
   a second side branch coupled to said main body, said second side branch comprising at least one module couple to a support wire,
   wherein said first side branch and said second side branch are coupled to each other at an apex section of the bifurcated stent and the bifurcated stent is inserted into a body lumen in a closed configuration with an axis of said first side branch and an axis of said second side branch substantially parallel to each other.

2. A bifurcated stent as defined in claim 1, wherein each of said modules defines a closed circumferential loop and said modules are arranged on said respective support wire to define a generally tubular configuration.

3. A bifurcated stent as defined in claim 1, wherein each of said modules is expandable from a radially contracted configuration in which it can be positioned in the body lumen to a radially expanded configuration.

4. A bifurcated stent as defined in claim 1, wherein each of said modules is formed from a serpentine wire having a plurality of elongate segments alternated with shorter connective bends.

5. A bifurcated stent as defined in claim 4, wherein said serpentine wire has free terminal ends attached to a connector to secure each of said modules in its closed circumferential loop configuration.

6. A bifurcated stent as defined in claim 1, wherein said modules are coupled to said support wire using connectors.

7. A bifurcated stent as defined in claim 6, wherein each of said modules, support wire, and connectors are formed from a material sufficiently similar in composition to inhibit development of corrosion at junctures where said modules, support wire, and connectors join each other.

8. A bifurcated stent as defined in claim 6, further comprising spacers disposed between adjacent connectors.

9. A bifurcated stent as defined in claim 8, wherein said spacers and said connectors are formed of the same material and define a substantially continuous region of high radiopacity when visualized radiographically.

10. A bifurcated stent as defined in claim 4, wherein said serpentine wire and said support wire have a different malleability.

11. A bifurcated stent as defined in claim 4, wherein said serpentine wire is formed from a material belonging to the group comprising annealed stainless steel, titanium alloys, nickel gold alloys, nickel chromium alloys, and titanium chromium alloys.

12. A bifurcated stent as defined in claim 1, wherein said first side branch comprises a plurality of modules and said second side branch comprises a plurality of modules.

13. A bifurcated stent as defined in claim 1, wherein said support wire of said first side branch comprises an extension of said support wire of said main body and said first side branch is coupled to said main body through said support wire.

14. A bifurcated stent as defined in claim 13, wherein each of said modules of said first side branch are coupled to said support wire.

15. A bifurcated stent as defined in claim 14, wherein said modules of said first side branch are coupled to said support wire using connectors.

16. A bifurcated stent as defined in claim 14, wherein each of said modules of said first branch is formed from a serpentine wire having a plurality of elongate segments alternated with shorter connective bends.

17. A bifurcated stent as defined in claim 16, wherein said serpentine wire has free terminal ends attached to a connector to secure each of said modules in its closed circumferential loop configuration.

18. A bifurcated stent as defined in claim 1, wherein each of said modules of said main body is coupled to at least two support wires and one of said at least two support wires extends to said first side branch to form said support wire of said first side branch and another of said at least two support wires extends to said second side branch to form said support wire of said second branch.

19. A bifurcated stent as defined in claim 1, wherein the stent is coated with a protective material.

20. A bifurcated stent as defined in claim 19, wherein said protective material comprises carbon.

21. The bifurcated stent of claim 18, wherein said support wires extending from said main body to said first side branch and said second side branch each terminate at a first module of each of said first side branch and said second side branch and said first and second side branches are coupled to each other utilizing a third support wire coupled to a plurality of modules of said first and second side branches and extending into said apex section of the stent.

* * * * *